US011076988B2

(12) United States Patent
Ghannoum et al.

(10) Patent No.: US 11,076,988 B2
(45) Date of Patent: Aug. 3, 2021

(54) ENHANCING PERFORMANCE OF A CAPSULOTOMY DEVICE

(71) Applicant: Alcon Inc., Fribourg (CH)

(72) Inventors: Ziad R. Ghannoum, Trabuco Canyon, CA (US); Guangyao Jia, Irvine, CA (US); Sean Christopher Madden, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 646 days.

(21) Appl. No.: 15/654,061

(22) Filed: Jul. 19, 2017

(65) Prior Publication Data
US 2018/0036170 A1 Feb. 8, 2018

Related U.S. Application Data

(60) Provisional application No. 62/369,871, filed on Aug. 2, 2016.

(51) Int. Cl.
| *A61F 9/007* | (2006.01) |
| *A61B 18/14* | (2006.01) |
| *A61F 9/008* | (2006.01) |
| *A61B 10/02* | (2006.01) |

(52) U.S. Cl.
CPC ...... *A61F 9/00754* (2013.01); *A61F 9/00763* (2013.01); *A61B 10/0266* (2013.01); *A61B 10/0275* (2013.01); *A61B 2018/141* (2013.01); *A61B 2018/1407* (2013.01); *A61F 2009/00889* (2013.01)

(58) Field of Classification Search
CPC .. A61F 9/007; A61F 9/00754; A61F 9/00763; A61F 2009/00885; A61F 2009/00887; A61F 2009/00889; A61B 10/0266; A61B 10/0275; A61B 2018/1407; A61B 2018/141
See application file for complete search history.

(56) References Cited

U.S. PATENT DOCUMENTS

| 5,171,314 | A | * | 12/1992 | Dulebohn | ........ | A61B 17/32056 606/110 |
| 8,814,854 | B2 | | 8/2014 | Jia et al. | | |
| D737,438 | S | | 8/2015 | Ghannoum | | |
| 9,125,720 | B2 | | 9/2015 | Jia et al. | | |
| 2003/0135222 | A1 | * | 7/2003 | Baska | ..................... | A61B 18/14 606/113 |
| 2006/0100617 | A1 | | 5/2006 | Boukhny | | |
| 2010/0094278 | A1 | | 4/2010 | Jia et al. | | |
| 2010/0312252 | A1 | | 12/2010 | Jia et al. | | |
| 2012/0245583 | A1 | * | 9/2012 | Truckai | ................ | A61B 18/042 606/41 |
| 2015/0216728 | A1 | | 8/2015 | Keller | | |

FOREIGN PATENT DOCUMENTS

| CN | 202699235 U | 1/2013 |
| CN | 107072814 A | 8/2017 |
| WO | 2010/141179 A1 | 12/2010 |
| WO | 2010/141181 A1 | 12/2010 |

* cited by examiner

*Primary Examiner* — Ronald Hupczey, Jr.
*Assistant Examiner* — Bradford C. Blaise

(57) ABSTRACT

The present disclosure provides a capsulotomy device having a unique insertion sleeve configuration comprising beveling and two notches at the distal end of the insertion sleeve. The unique configuration assures that the motion the capsulotomy loop comprising the heating element goes through during deployment from and retraction into the insertion sleeve is minimized and predictable.

18 Claims, 7 Drawing Sheets

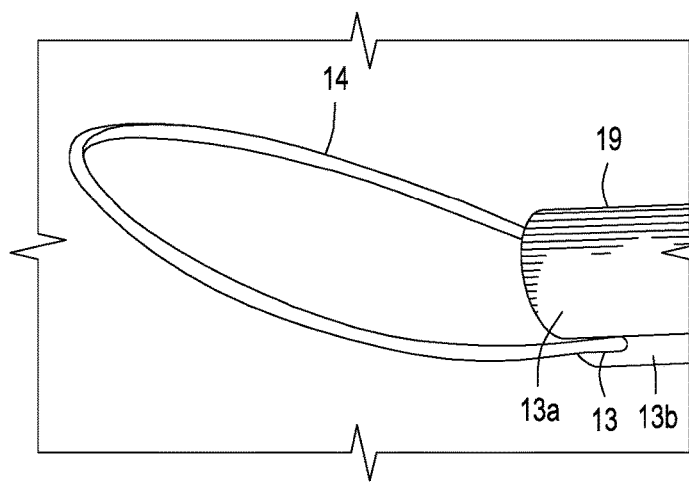
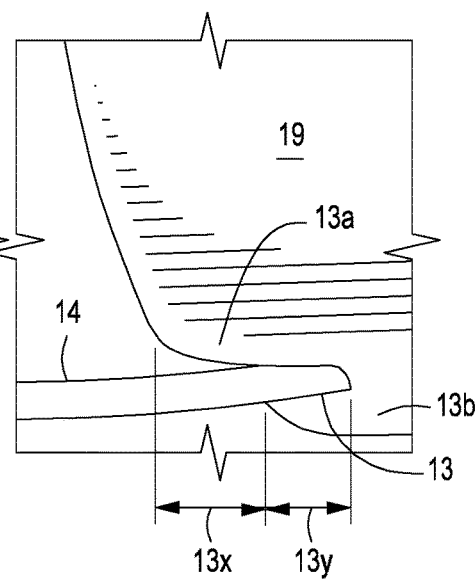
FIG. 2A
FIG. 2B

ENHANCING PERFORMANCE OF A CAPSULOTOMY DEVICE

PRIORITY CLAIM

This application claims the benefit of priority of U.S. Provisional Patent Application Ser. No. 62/369,871 titled "Enhancing Performance of a Capsulotomy Device", filed on Aug. 2, 2016, whose inventors are Ziad R. Ghannoum, Guangyao Jia, and Sean Christopher Madden, which is hereby incorporated by reference in its entirety as though fully and completely set forth herein.

FIELD OF THE INVENTION

The field of the invention is drawn to improvements to the design of a capsulotomy device.

BACKGROUND OF THE INVENTION

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

An accepted procedure for the treatment of cataracts is surgical removal of the lens (e.g., through phacoemulsification) and replacement of the lens function by an artificial intraocular lens. Prior to removing the cataractous lens, an opening, or rhexis, may be made in the anterior capsule. During phacoemulsification, there may be tension on the cut edges of the anterior capsularhexis while the lens nucleus is emulsified. Further, if the capsule is opened with numerous small capsular tears, the small tags that remain may lead to radial capsular tears that may extend into the posterior capsule. A radial tear may constitute a complication since it may destabilize the lens for further cataract removal and safe intraocular lens placement within the lens capsule later in the operation. In addition, if the posterior capsule is punctured, the vitreous may gain access to the anterior chamber of the eye. If this happens, the vitreous may need to be removed by an additional procedure with special instruments. The loss of vitreous may lead to subsequent retinal detachment and/or infection within the eye. Further, while some ophthalmic procedures may also require a posterior capsularhexis, current devices designed for anterior capsularhexis may not have an optimal geometry for performing a posterior capsularhexis.

There is accordingly a need for improving the performance of capsulotomy devices to minimize the risk of capsular tears and to minimize and make predictable the motion of the loop of the capsulotomy device in the interior of the eye.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

One embodiment of the present disclosure provides a capsulotomy device having a unique insertion sleeve configuration comprising beveling and two notches at the distal end of the insertion sleeve. Generally, one embodiment provides a capsulotomy device comprising a tubular insertion sleeve beveled at a distal end of the tubular insertion sleeve and further comprising two notches disposed opposite one another at the distal end of the tubular insulation sleeve, where a top portion of each notch extends further distally (toward the end where a loop is inserted into the eye) than the bottom portion of each notch; an insulating portion slidably disposed within the tubular insertion sleeve, where the insulating portion at a distal end comprises an electrically insulating material separating first and second ends of a heating element; and a substantially planar loop comprising the heating element coupled to the distal end of the insulating portion, where the first and second ends of the heating element define a transitional neck that extends at an upward angle from the substantially planar loop, and wherein the substantially planar loop is disposed within the two notches when deployed and retracted from the tubular insertion sleeve.

In some aspects of this embodiment, proximal ends of the notches are vertically asymmetrically offset at the distal end of the tubular insulation sleeve; for example, the proximal ends of the notches may be vertically asymmetrically offset 0.20-0.60 mm, 0.25-0.50 mm, or 0.30-0.40 mm. Other offsets are also contemplated.

In some aspects of an embodiment, the heating element is a resistive heating element, and in some aspects, the resistive heating element is formed of a nickel titanium alloy.

In some aspects of an embodiment, a distal end of the bottom portion of each notch is recessed 0.30-1.00 mm, 0.40-0.80 mm, or 0.50-0.70 mm from a distal end of the top portion of each notch. Other recessed dimensions are also contemplated. Also in some aspects of this embodiment, a distal end of the bottom portion of each notch is 0.25-0.75 mm, 0.30-0.60 mm, or 0.40-0.50 mm from a proximal end of each notch. Other dimensions for the distal end of the bottom portion of each notch are also contemplated.

Also in some aspects, the loop has a bottom face for placing against an anterior lens capsule or a posterior lens capsule of an eye, a top face opposite the bottom face, where the heating element further comprises a thermally insulating layer disposed on at least the top face of the loop but absent from the bottom face of the loop.

Another embodiment provides a method where the insulating layer is deposited on the heating element by vapor deposition or other coating methods, and the insulating layer is removed from the bottom face of the loop by laser ablation.

Yet another embodiment provides a loop having an elliptical shape before deployment in an eye, and wherein the loop has a round shape after deployment in the eye.

Yet another embodiment provides a capsulotomy device comprising a tubular insertion sleeve beveled at a distal end of the tubular insertion sleeve and further comprising two notches disposed opposite one another at the distal end of the tubular insulation sleeve, where proximal ends of the notches are vertically asymmetrically offset at the distal end of the tubular insulation sleeve, and where a top portion of each notch extends further distally than the bottom portion of each notch. These and other aspects and uses of the various embodiments will be described in the detailed description.

BRIEF DESCRIPTION OF THE FIGURES

FIGS. 2A-B illustrate the "shark mouth" notch configuration of an insertion sleeve with the loop partially retracted, according to an embodiment.

FIG. 4A shows the "shark mouth" notches symmetrically placed in the insertion sleeve, and FIG. 4B shows the "shark mouth" notches asymmetrically placed in the insertion sleeve, according to various embodiments.

DETAILED DESCRIPTION OF THE INVENTION

Before the present capsulotomy devices are described, it is to be understood that the disclosure is not limited to the specific embodiments described, as such may, of course, vary. It is also to be understood that the terminology used herein is for the purpose of describing particular aspects only and is not intended to limit the scope of the present disclosure, which will be limited only by the appended claims.

Note that as used in the present specification and in the appended claims, the singular forms "a," "an," and "the" include plural referents unless the context clearly dictates otherwise. Unless defined otherwise, all technical and scientific terms used herein have the same meaning as commonly understood by one of ordinary skill in the art of the present field.

Where a range of values is provided, it is understood that each intervening value between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes both of the limits, ranges excluding either of those included limits are also included in the disclosure.

In the following description, numerous specific details are set forth to provide a more thorough understanding of the present disclosure. However, it will be apparent to one of skill in the art upon reading the specification that the present disclosure may be practiced without one or more of these specific details. In other instances, features and procedures well-known to those skilled in the art have not been described in order to avoid obscuring the disclosure.

U.S. patent application entitled "CAPSULARHEXIS DEVICE," Publication No. 20060100617, Ser. No. 10/984,383, by Mikhail Boukhny filed Nov. 9, 2004 is hereby incorporated by reference in its entirety as though fully and completely set forth herein.

U.S. patent application entitled "CAPSULARHEXIS DEVICE WITH FLEXIBLE HEATING ELEMENT," Publication No. 2010/0094278, Ser. No. 12/249,982, by Glenn Sussman and Guangyao Jia filed Oct. 13, 2008 is hereby incorporated by reference in its entirety as though fully and completely set forth herein.

U.S. patent application entitled "CAPSULARHEXIS DEVICE WITH FLEXIBLE HEATING ELEMENT HAVING AN ANGLED TRANSITIONAL NECK," Publication No. 20100312252, Ser. No. 13/477,175, by Guangyao Jia and Glenn Sussman filed June 2009 is hereby incorporated by reference in its entirety as though fully and completely set forth herein.

U.S. patent entitled "CAPSULOTOMY REPAIR DEVICE AND METHOD FOR CAPSULOTOMY REPAIR," U.S. Pat. No. 8,814,854, by Guangyao Jia and Glenn Sussman filed Apr. 5, 2010 is hereby incorporated by reference in its entirety as though fully and completely set forth herein.

Figure 1A:
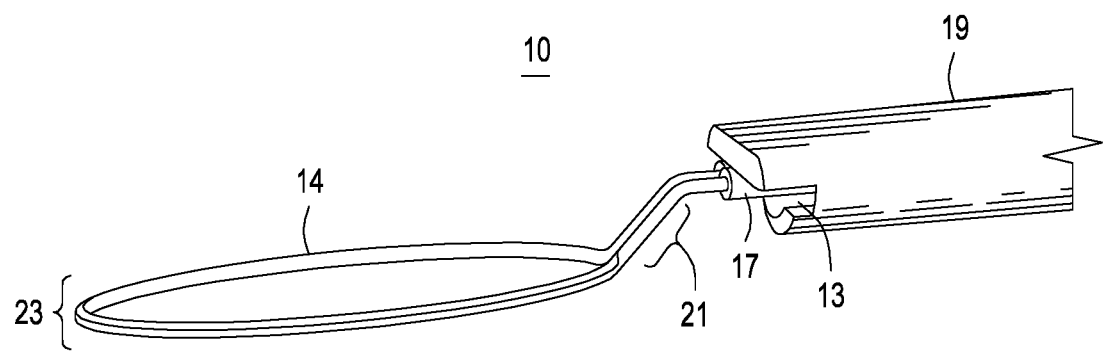
FIGS. 1A-B illustrate two positions of a capsulotomy device according to an embodiment.
Figure 1B:
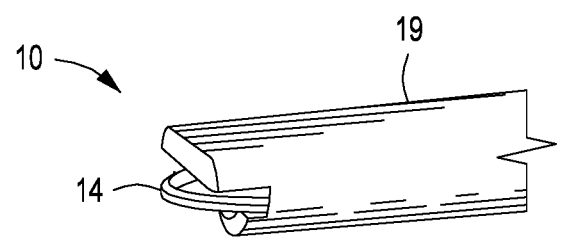

FIGS. 1A-B show a plan view of embodiments of a capsularhexis device 10. Those skilled in the art will appreciate that FIGS. 1A-B, like the several other attached figures, are not to scale, and that several of the features may be exaggerated to more clearly illustrate various features. Those skilled in the art will also appreciate that the illustrated structures are only exemplary, and not limiting. In some embodiments, the capsulotomy device 10 may include a substantially circular, flexible loop 23 comprising a resistive-heating element 14 that may be energized to produce localized heating on an anterior lens capsule 509 and/or posterior lens capsule 513 (e.g., see FIG. 5) of an eye 32 to create a through-cut or define a weakened boundary for detachment of a portion of the capsule 36 within the loop 23. The capsulotomy device 10 may be positioned within the anterior chamber 34 of the eye 32 through a small incision 505 to perform a capsulotomy. This procedure may facilitate, for example, phacoemulsification of a cataractous lens and insertion of an artificial intraocular lens (OIL).

Figure 5:
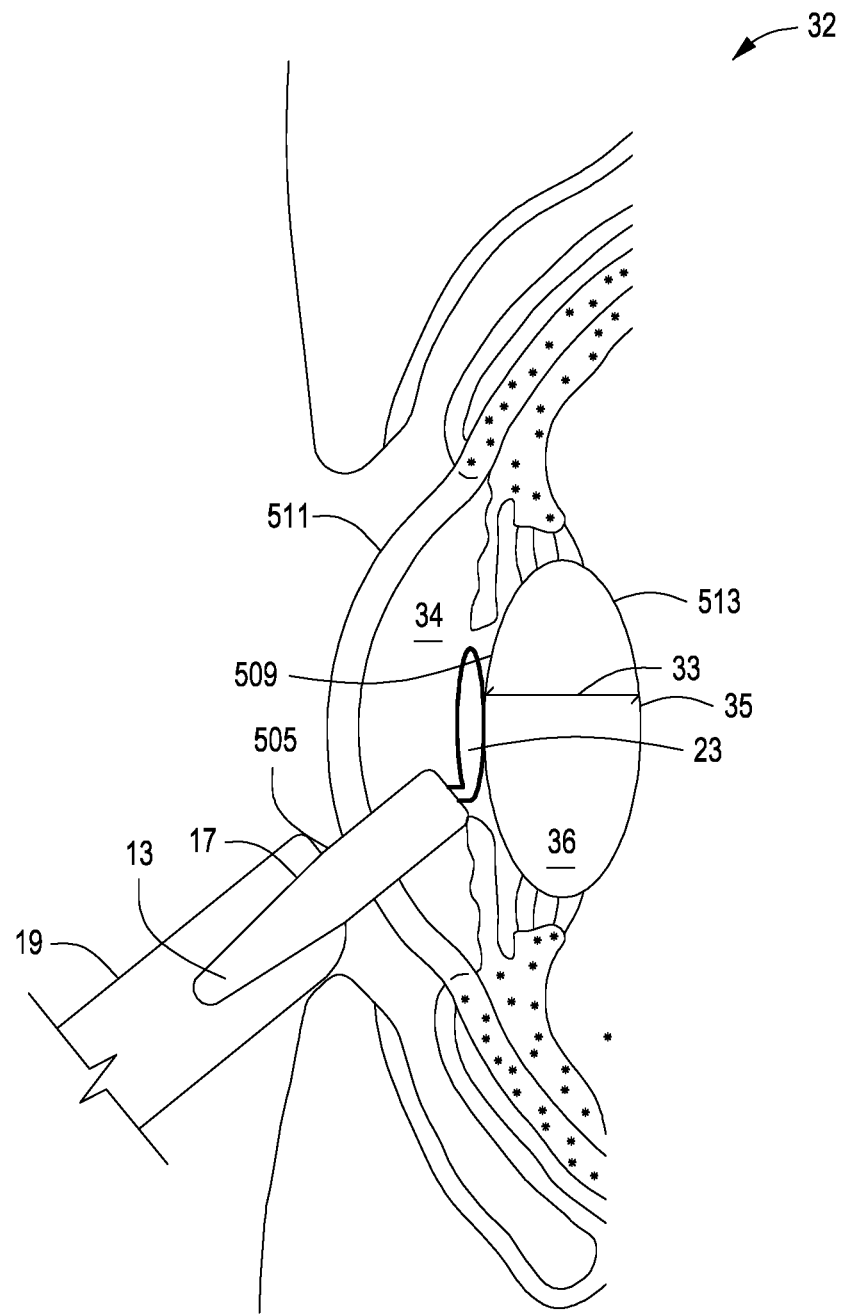
FIG. 5 illustrates a side view of the capsulotomy device positioned on the anterior surface of the capsule, according to an embodiment.

As seen in FIG. 1A, in various embodiments the heating element 14 of loop 23 may include a transitional neck 21, e.g., formed by first and second wire ends with an offsetting bend so as to offset a planar face of the loop 23 below a centerline of an insertion sleeve 19. The wire ends forming transitional neck 21 bend away from the centerline. Bending away from the centerline allows the substantially planar loop 23 to be placed more parallel with the anterior and/or posterior capsule face. As seen in FIG. 5, the wire ends in the transitional neck 21 may displace the substantially planar loop 23 a depth 33 of the capsule 36 to position the loop 23 for uniform contact with the posterior capsule face 35. In some embodiments, the diameter of the loop 23 may be adjusted according to whether the loop 23 will be used in an anterior capsulotomy or a posterior capsulotomy, which may use a smaller diameter loop, e.g., approximately in a range of 2-4 millimeters (mm) than in anterior capsulotomy which may use a loop having a diameter approximately in a range of 4-6 mm. Other diameters are also contemplated. Further, the geometry of the offsetting bend of the transitional neck 21 of the loop 23 may be adjusted based on whether the loop 23 will be used for posterior capsulotomy or anterior capsulotomy. In some embodiments, the transitional neck 21 may have a length (a distance from the insulating portion 17 to the loop 23) of approximately 1-2 mm; however, other lengths are also contemplated.

According to several embodiments, the resistive-heating element 14 of loop 23 may include an at least partially bare resistance-heating element made from a super-elastic wire. By combining the super-elasticity of the wire material with a relatively high electric resistivity, a collapsible, substantially planar ring-shaped loop 23 is constructed to perform capsulotomy by localized heating. Because the loop 23 is collapsible, the loop 23 is easily inserted into the eye 32 through a small incision 505 (e.g., ~2 mm) in the cornea 511. Other incision sizes and locations are also contemplated.

In some embodiments, the loop 23 may be formed from a nickel titanium alloy, such as Nitinol, which exhibits superelastic and shape memory properties. Because the loop 23 is superelastic (which term is intended herein as a synonym for the somewhat more technically precise term "pseudoelastic"), the loop 23 is able to withstand a significant amount of deformation when a load is applied and then return to its original shape when the load is removed. (Those skilled in the art will appreciate that this property is distinct from, although related to, "shape memory", which refers to a property exhibited by some materials in which an object that is deformed while below the material's transformation temperature returns to its former shape when warmed to above the transformation temperature. Nitinol exhibits both properties; superelasticity is exhibited above the transformation temperature.) Further, Nitinol is resistive and can thus be heated with an electrical current, making it useful for forming the resistive-heating element 14. Of course, those skilled in the art will appreciate that other materials that are resistive and superelastic may be used instead of Nitinol in some embodiments.

Because of its superelastic properties, the loop 23 is collapsed for insertion into the anterior chamber 34 of the eye 32, regaining its pre-defined shape upon deployment within the anterior chamber 34. A collapsed loop 23 in a retracted position in the insertion sleeve 19 is shown in FIG. 1B. The loop 23 is collapsible upon retraction into the insertion sleeve 19 and expandable to its original shape upon ejection or deployment from the insertion sleeve 19.

The ends of the resistive-heating element 14 form a lead section, where the wires of resistive-heating element 14 are kept electrically separate with a flexible, electrically insulating portion 17. In some embodiments, the insulating portion 17 may surround a portion of the lead section. However, those skilled in the art will appreciate that the insulating portion 17 may surround only one lead, or may only partially surround either or both leads, in some embodiments, provided that the two leads extending away from the loop 23 and into the insertion sleeve 19 may be kept electrically separate so that electrical current may be passed through the loop 23. Insulating portion 17 may include a bio-compatible and high temperature-resistant material, such as polyimide or Teflon™. In some embodiments, insulating portion 17 may be flexible.

In some embodiments, insertion sleeve 19 includes a flat or cylindrical tube that slidably engages the insulating portion 17. In the present embodiment, the insertion sleeve 19 forms a slip-fit with the insulating portion 17. Insertion sleeve 19 is used to house the loop 23, where the loop 23 is deployed into the eye 32 during the capsulotomy procedure and the loop 23 is retracted back into insertion sleeve 19 after the capsulotomy procedure. The insertion sleeve 19, which may be made from a thermoplastic, also contains electrical connectors and/or connecting wires so that the heating element 14 of loop 23 may be selectively connected to a power source for heating. In some embodiments, the insertion sleeve 19, insulation material 17, and loop 23 form a disposable unit that can be selectively connected during use to a handpiece or other apparatus that can supply electrical current.

FIGS. 2A-B illustrate a configuration for the distal end of insertion sleeve 19—that is, the end of insertion sleeve 19 that is inserted into the eye. FIG. 2A shows a "shark mouth" notch configuration of the insertion sleeve 19 with the loop 23 partially retracted. The "shark mouth" configuration of the notch 13 shows the distal end of the bottom portion 13b of insertion sleeve 19 recessed as compared to the distal end of the top portion 13a of insertion sleeve 19, and the distal surfaces of the notch 13 are beveled. The distance that the distal end of the bottom portion 13b is recessed from the distal end of the top portion 13a (distance 13x as seen in FIG. 2B) may be from 0.30-1.00 mm, or from 0.40-0.80 mm, or in many embodiments, from 0.50-0.70 mm. Other distances 13x are also contemplated. The notch 13 can be of any configuration, as long as the distal end of the bottom portion 13b of insertion sleeve 19 is recessed as compared to the distal end of the top portion 13a of insertion sleeve 19, the distal surfaces of notch 13 are beveled, and that loop 23 is able to be deployed from and retracted into insertion sleeve 19. FIG. 2B shows a distance 13y, measured from the distal end of bottom portion 13b of notch 13 to the proximal end of notch 13, which distance 13y may be from 0.25-0.75 mm, or from 0.30-0.60 mm, or in many embodiments, from 0.40-0.50 mm. Other distances 13y are also contemplated. The "shark mouth" configuration (encompassing both the distal end of the bottom portion 13b of insertion sleeve 19 being recessed as compared to the distal end of the top portion 13a of insertion sleeve 19 and the distal surfaces of the notch 13 being beveled) of notch 13 allows a minimized and predictable motion of the loop 23 during deployment from and retraction into insertion sleeve 19. As seen in FIG. 2A, when the transitional neck portion 21 of loop 23 is deployed from or retracted into insertion sleeve 19, the loop 23 may be bent upward; that is, the distal portion of the loop 23 may be elevated. However, because of the "shark mouth" configuration of insertion sleeve 19, the elevation of loop 23 is reduced as compared to prior art versions of the insertion sleeve, which prevents inadvertent contact of the capsulotomy device with the cornea.

Figure 3A:
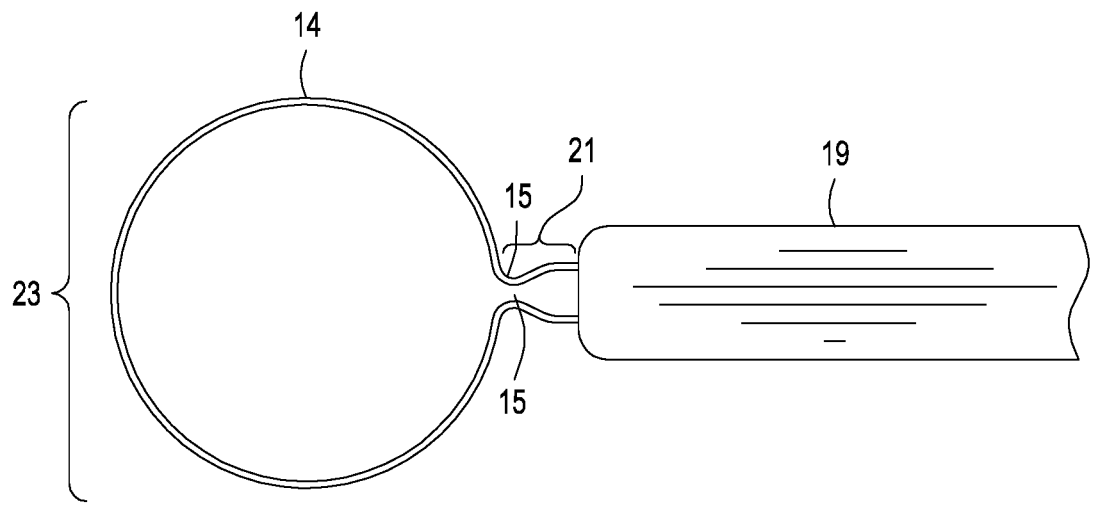
FIG. 3A is a top view of the distal portion of a capsulotomy device according to an embodiment.
Figure 3B:
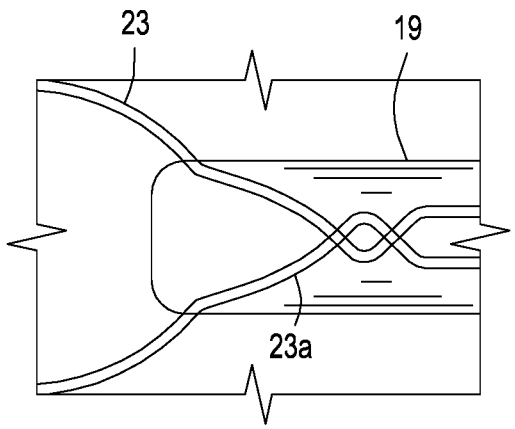
FIG. 3B is a top view of the distal portion of a capsulotomy device according to an embodiment where the loop is partially retracted into the insertion sleeve.
Figure 3C:
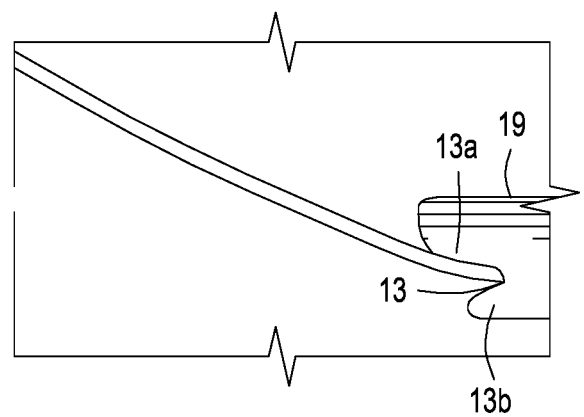
FIG. 3C is a side view of the insertion sleeve from FIG. 3B illustrating the "shark mouth" notch configuration, according to an embodiment.
Figure 3D:
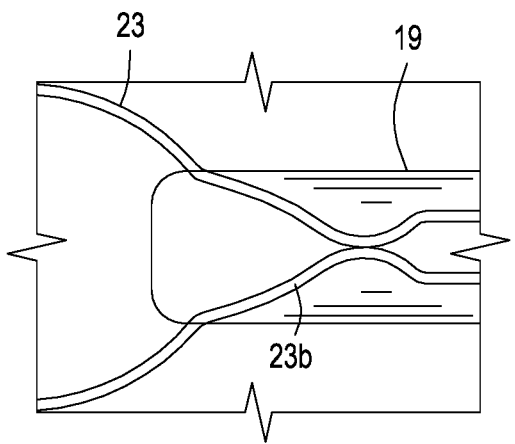
FIG. 3D is a top view of the distal portion of a capsulotomy device according to an embodiment where the loop is partially retracted into the insertion sleeve.
Figure 3E:
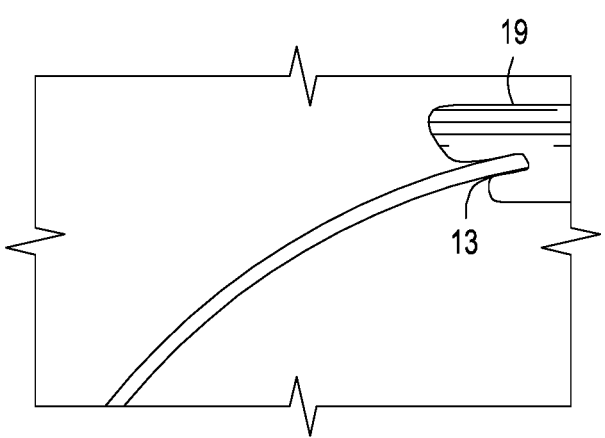
FIG. 3E is a side view of the insertion sleeve from FIG. 3D illustrating the "shark mouth" notch configuration, according to an embodiment.

FIGS. 3A-E show various features of the insertion sleeve 19, according to an embodiment. FIG. 3A is a top view of the distal portion of a capsulotomy device, showing substantially planar loop 23 comprising resistive-heating element 14 and an elbow 15 of the transitional neck 21 and insertion sleeve 19 (where in this top view of insertion sleeve 19, notch 13 cannot be seen). FIG. 3B is a top view of the distal portion of a capsulotomy device where the loop 23 is partially retracted into the insertion sleeve 19 (the insertion sleeve 19 is shown in this figure as being transparent). When the loop 23 is collapsed during retraction, the loop 23 folds such that portions of the loop 23 cross one another 23a. FIG. 3C shows a side view of the insertion sleeve 19 from FIG. 3B where the insertion sleeve 19 is transparent. FIG. 3C illustrates the "shark mouth" notch 13 configuration of insertion sleeve 19. In some embodiments, the "shark mouth" notch 13 configuration includes a distal end of the bottom portion 13b of notch 13 being recessed as compared to the distal end of the top portion 13a of notch 13. In some embodiments, the "shark mouth" notch 13 configuration further includes the distal surfaces of the notch 13 being beveled. Further, in some embodiments, the "shark mouth" notch 13 configuration includes the elevation of loop 23. FIG. 3D, like FIG. 3B, is a top view of the distal portion of a capsulotomy device where the loop is partially retracted into the insertion sleeve; however, in FIG. 3D, the portion of the loop 23 that is collapsed into insertion sleeve 19 during retraction does not show portions of the loop 23 crossing one another as seen in FIG. 3B. That is, the portions of loop 23 that are shown retracted into insertion sleeve 19 in FIG. 3D do not cross one another 23b. FIG. 3E is a side view of the insertion sleeve from FIG. 3D illustrating the "shark mouth" notch configuration; however, the result of the failure of the portions of loop 23 not crossing one another 23b is that the loop 23 may point down during retraction of the loop 23 into insertion sleeve 19, which may lead to inadvertent contact of the loop 23 with the lens capsule.

Figure 4A:
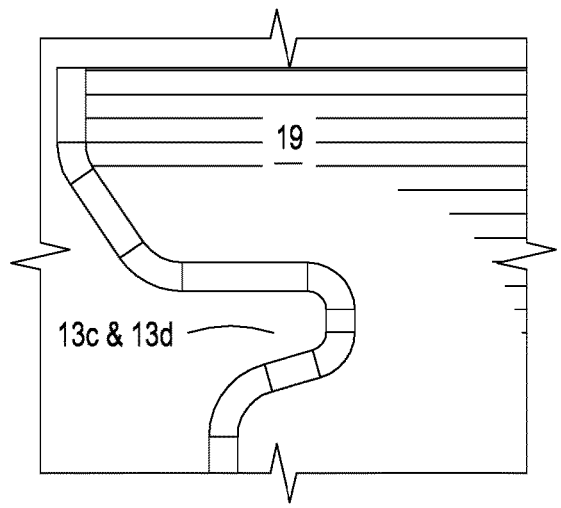
FIGS. 4A-B illustrate the "shark mouth" notch configuration in a side view of the insertion sleeve, where
Figure 4B:
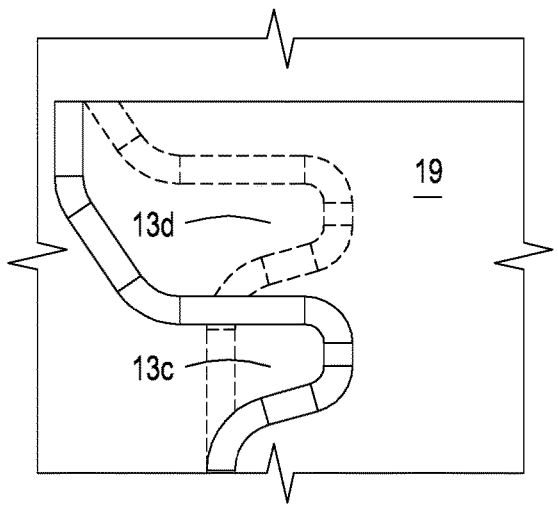

To ensure that portions of the loop 23 cross one another (such as at 23a in FIG. 3B) when the loop 23 is collapsed during retraction (and thus ensuring the loop 23 does not point down), the notches 13 on either side of insertion sleeve 19 are configured to have a vertical offset from one another. This feature is illustrated in FIGS. 4A-B. FIGS. 4A-B illustrate the "shark mouth" notch configuration of the insertion sleeve, where FIG. 4A shows the two "shark mouth" notches 13c and 13d on either side of insertion sleeve 19 symmetrically placed in the insertion sleeve, such that when viewed from the side of insertion sleeve 19, notches 13c and 13d are aligned. This symmetrical configuration of notches 13c and 13d may lead to the failure of the portions of the loop 23 that have been retracted into insertion sleeve 19 to cross one another, leading further to loop 23 pointing down during retraction of the loop 23 (as seen in FIG. 3E). However, FIG. 4B shows the "shark mouth" notches 13c and 13d having a vertical offset from one another as placed in the insertion sleeve 19 (with notch 13c being seen from the side of insertion sleeve 19, and notch 13d being seen in relief); that is, "shark mouth" notches 13c and 13d are asymmetrically positioned vertically relative to one another in the insertion sleeve 19, which leads to the retracted portions of loop 23 crossing one another (as seen in FIG. 3C) resulting in elevation of loop 23 during retraction. Thus, in some embodiments, the vertical offset of the proximal ends of the notches may be from 0.20-0.60 mm, or from 0.25-0.50 mm, or in many embodiments, from 0.30-0.40 mm. Other vertical offsets are also contemplated. Thus, embodiments of the "shark mouth" notch configuration of insertion sleeve 19 encompasses 1) the distal end of the bottom portion 13b of insertion sleeve 19 being recessed as compared to the distal end of the top portion 13a of insertion sleeve 19 (as seen in FIG. 1A, FIGS. 2 A-B, and FIGS. 3C and E); 2) the distal surfaces of the notch 13 being beveled (as seen in FIG. 1A, FIGS. 2A-B, and FIGS. 3C and 3E); and 3) the proximal ends of notches 13c and 13d being vertically asymmetrically offset from one another at the distal end of insertion sleeve 19 (as seen in FIG. 4B).

FIG. 5 illustrates a side view of an embodiment of a capsulotomy device positioned upon the anterior capsule of the eye. FIG. 5 shows the distal end of the capsulotomy device comprising insertion sleeve 19 having a "shark mouth" notch 13, flexible insulating portion 17, and loop 23 having transitional neck 21. Also seen in FIG. 5 is anterior chamber 34 of the eye 32, posterior lens capsule 513 of the eye 32, anterior lens capsule 509 of the eye 32, cornea 511, and insertion 505 (through which insulating portion 17 is inserted).

Figure 6A:
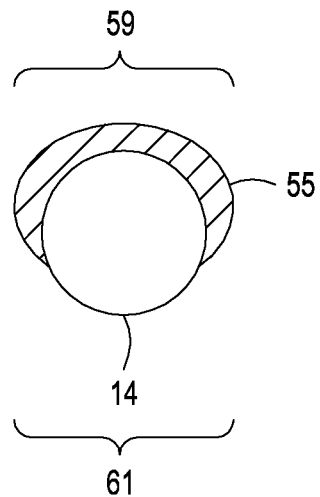
FIGS. 6A-B illustrate alternate configurations of the wire used in the capsulotomy device according to various embodiments.
Figure 6B:
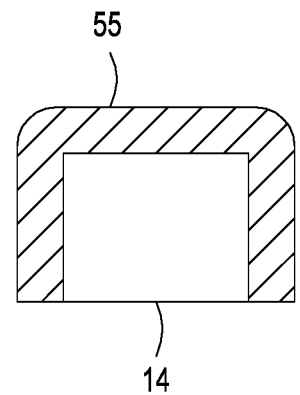

The capsulotomy device may work in the presence of viscoelastic materials that are typically used in cataract surgery. Viscoelastic materials work as a thermal insulator to keep the thermal energy from rapid dissipation into the anterior chamber through the top portion of the loop surface (e.g., the surface of the loop that is not in contact with the lens capsule). To eliminate the impact of the variations in viscoelastic materials on the cutting performance of the device, the top portion of the resistive-heating element 14 can be coated with a thermal insulation layer (e.g., parylene ((poly)p-xylene) polymer, or Teflon™) that is sufficiently thick to keep the loop temperature constant in different Ophthalmic Viscosurgical Devices (OVDs) or even in eye humor. Other coating materials for the thermal insulation layer are also contemplated. Turning to FIG. 6A, in some embodiments, to reduce any potential effects on tissue near the loop 23, a thermally insulating layer may be disposed on at least a top face of the loop 23, such that a bottom face, which may be disposed against the capsule 36 during the capsulotomy procedure, may be left bare. In some embodiments, the capsulotomy device cuts the lens capsule by localized cauterization; therefore, the cutting performance of the device may be at least partially dependent on the heat transfer conditions between the resistive-heating element 14 of loop 23 and the lens capsule. A cross-sectional view of one such embodiment is shown in FIG. 6A, which shows a cross-section of heating element 14, partially surrounded with a thermally insulating layer 55. In some embodiments, the resistive-heating element 14 may have a square or rectangular cross-section, as shown in FIG. 6B, in which case insulation 55 may be disposed on three sides of the resistive-heating element 14. In either case, insulation 55 may be disposed on the heating element 14 around all or substantially all of the loop 23.

Figure 6C:
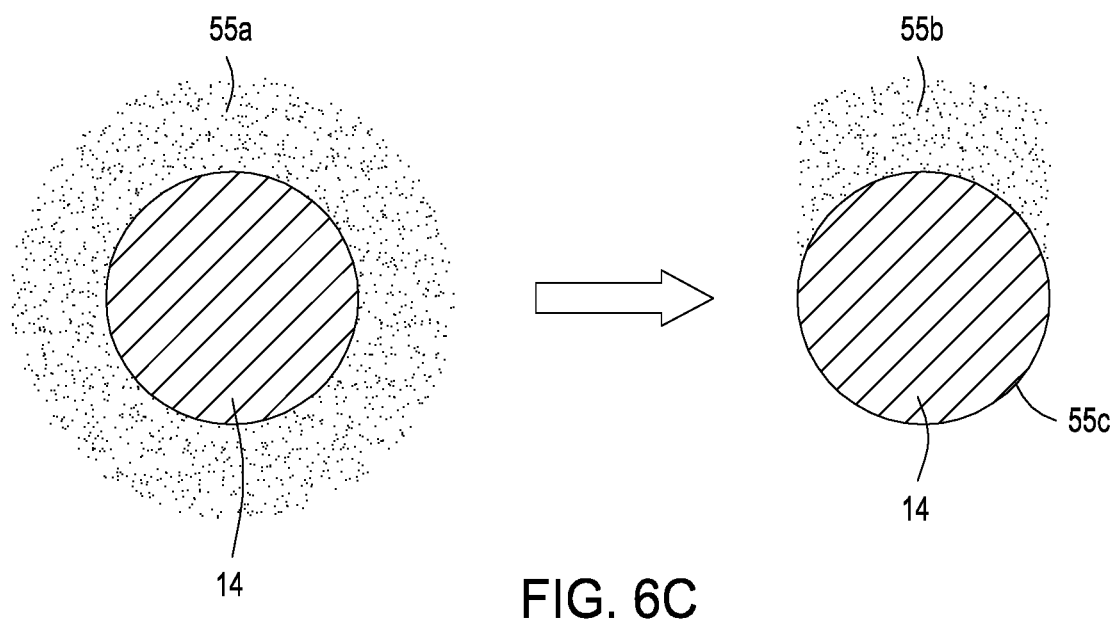
FIG. 6C shows an embodiment of a method of forming the alternate configurations of the wire shown in FIGS. 6A-B.

FIG. 6C shows a method for depositing a thermal insulating layer on loop 23.

First, the heating element 14 may be coated entirely with, e.g., parylene 55a by, e.g., vapor deposition. The coating step may then be followed by, e.g., laser ablation to remove the parylene from the bottom side of heating element 14 (55c) exposing the cutting surface of heating element 14, but leaving the top surface of heating element 14 coated with parylene (55b).

Figure 7A:
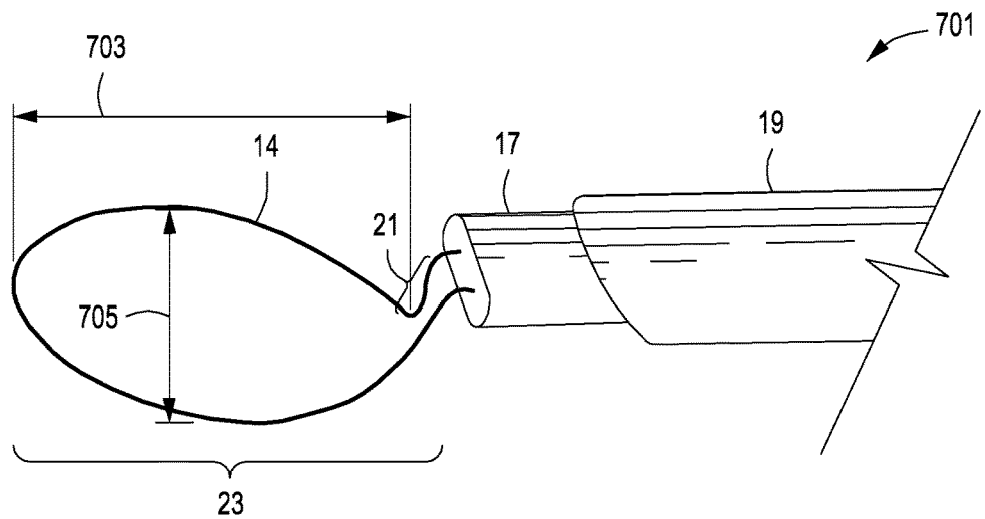
FIG. 7A illustrates a capsulotomy device according to various embodiments.
Figure 7B:
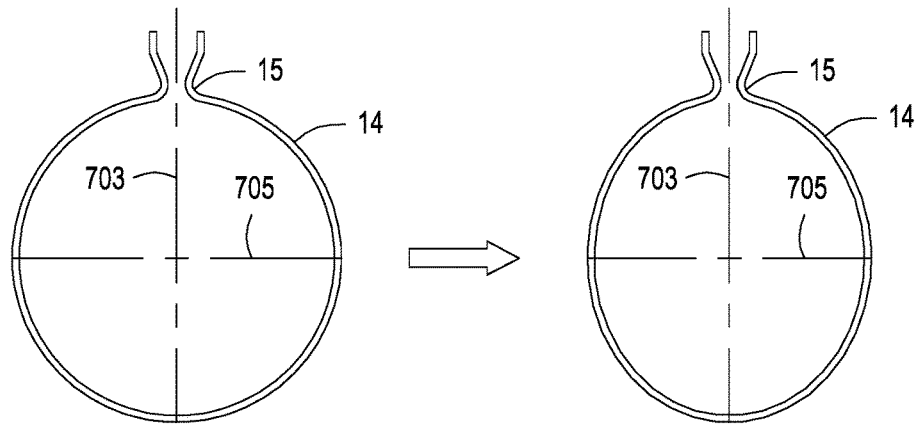
FIG. 7B shows the loop of a capsulotomy device according to the prior art.
Figure 7C:
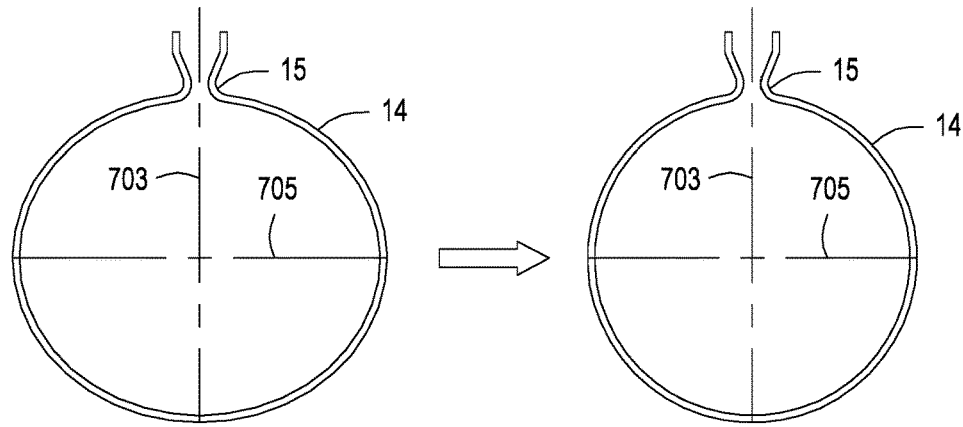
FIG. 7C shows the loop of a capsulotomy device according to an embodiment.

FIG. 7A illustrates a capsulotomy device having insertion sleeve 19, electrically insulating portion 17, and substantially planar loop 23 having transitional neck 21, a length 703, and a width 705. FIG. 7B shows the substantially planar loop of a capsulotomy device according to the prior art, where the loop 23 has a substantially round configuration; that is length 703 and width 705 are substantially equal. Although loop 23 is made of Nitinol or another superelastic material, loop 23 is still subject to deformation, and the strain generated in the loop 23 when it is collapsed into the insertion sleeve 19 may exceed the limit for full recovery into its original circular shape. Such deformation may compromise the circularity of the loop 23 and thus the circularity of the capsulotomy. That is, the circular loop may become more or less elliptical with the length 703 of the loop exceeding the width 705 of the loop due to deformation of the loop in the retracted position (e.g., see resulting deformed loop on right side of FIG. 7B). To reduce loop deformation and the impact of the deformation on the circularity of the capsulotomy, the loop 23 can be preset to an elliptical shape instead of a circular shape with the length 703 being smaller than the width 705. When the loop is collapsed into the insertion sleeve, the permanent deformation tends to elongate length 703 while shortening width 705. As a result, the preset length 703 is increased (i.e., further lengthened), and the preset width 705 is decreased (i.e., shortened) to desired dimensions when the loop is extended from the insertion sleeve in the eye. Thus, the elliptical loop 23 is reset to the desired circular shape prior to use by taking advantage of the deformation generated when the loop is collapsed within the insertion sleeve prior to deployment within the eye. FIG. 7C shows the loop of a capsulotomy device according to an embodiment where loop 23 has an elliptical configuration; that is, where length 703 is smaller than width 705 prior to deployment within the eye, with the loop 23 having a circular shape upon deployment (e.g., see deformed loop on the right side of FIG. 7C). For example for a Nitinol loop, in exemplary embodiments the dimensions may be 4.8 mm for length 703 and 5.0 mm for width 705 for use in anterior capsulotomy and 1.8 mm for length 703 and 1.9 mm for width 705 for use in posterior capsulotomy. Other dimensions for the length and width are also contemplated.

Various modifications may be made to the presented embodiments by a person of ordinary skill in the art. For example, although some of the embodiments are described above in connection with capsulotomy devices, the improvements can also be used with other thermal cutting surgical devices. Other embodiments will be apparent to those skilled in the art from consideration of the present specification and practice of the embodiments disclosed herein. It is intended that the present specification and examples be considered as exemplary only with a true scope and spirit of the disclosure being indicated by the following claims and equivalents thereof. Moreover, all statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

We claim:

1. A capsulotomy device comprising:
   a tubular insertion sleeve beveled at a distal end of the tubular insertion sleeve and further comprising two vertically asymmetrically offset notches disposed opposite one another at the distal end of the tubular insulation sleeve, each of the two notches terminating at the beveled distal end of the tubular insertion sleeve, each of the two notches having a first face and a second face, the first face opposite the second face, wherein the first face extends further distally than the second face;
   an insulating portion slidably disposed within the tubular insertion sleeve, wherein the insulating portion at a distal end comprises an electrically insulating material separating first and second ends of a heating element; and
   a planar loop comprising the heating element coupled to the distal end of the insulating portion, wherein the first and second ends of the heating element define a transitional neck that extends at an upward angle from the planar loop, and wherein the planar loop is disposed within the two notches and between the first and second faces of each notch when deployed and retracted from the tubular insertion sleeve, such that when the planar loop is retracted, retracted portions of the planar loop cross one another resulting in elevation of the planar loop with respect to the tubular insertion sleeve.

2. The capsulotomy device of claim 1, wherein the notches are vertically asymmetrically offset 0.20-0.60 mm.

3. The capsulotomy device of claim 1, wherein the heating element is a resistive heating element formed of a nickel titanium alloy.

4. The capsulotomy device of claim 1, wherein a distal end of a bottom portion of each notch is recessed 0.30-1.00 mm from a distal end of a top portion of each notch.

5. The capsulotomy device of claim 1, wherein a distal end of a bottom portion of each notch is 0.25-0.75 mm from a proximal end of each notch.

6. The capsulotomy device of claim 1, wherein the planar loop has a bottom face for placing against an anterior lens capsule or a posterior lens capsule of an eye, a top face opposite the bottom face, and wherein the heating element further comprises a thermally insulating layer disposed on at least the top face of the planar loop but absent from the bottom face of the planar loop.

7. The capsulotomy device of claim 6, wherein the insulating layer is deposited on the heating element by vapor deposition.

8. The capsulotomy device of claim 7, wherein the insulating layer is removed from the bottom face of the planar loop by laser ablation.

9. The capsulotomy device of claim 1, wherein the planar loop has an elliptical shape before deployment in an eye, and wherein the planar loop has a round shape after deployment in the eye.

10. A capsulotomy device comprising:
    a tubular insertion sleeve beveled at a distal end of the tubular insertion sleeve and further comprising two notches disposed opposite one another at the distal end of the tubular insulation sleeve, wherein proximal ends of the notches are vertically asymmetrically offset 0.20-0.60 mm with respect to each other at the distal end of the tubular insulation sleeve, each of the two notches terminating at the beveled distal end of the tubular insertion sleeve, each of the two notches having a first face and a second face, the first face opposite the second face, wherein the first face extends further distally than the second face;
    an insulating portion slidably disposed within the tubular insertion sleeve, wherein the insulating portion at a distal end comprises an electrically insulating material separating first and second ends of a heating element; and
    a planar loop comprising the heating element coupled to the distal end of the insulating portion, wherein the first and second ends of the heating element define a transitional neck that extends at an upward angle from the planar loop, and wherein the planar loop is disposed within the two notches and between the first and second faces of each notch when deployed and retracted from the tubular insertion sleeve, such that when the planar loop is retracted, retracted portions of the planar loop cross one another resulting in elevation of the planar loop with respect to the tubular insertion sleeve.

11. The capsulotomy device of claim 10, wherein the heating element is a resistive heating element formed of a nickel titanium alloy.

12. The capsulotomy device of claim 10, wherein a distal end of a bottom portion of each notch is recessed 0.30-1.00 mm from a distal end of a top portion of each notch.

13. The capsulotomy device of claim 10, wherein a distal end of a bottom portion of each notch is 0.25-0.75 mm from a proximal end of each notch.

14. The capsulotomy device of claim 10, wherein the planar loop has a bottom face for placing against an anterior lens capsule or a posterior lens capsule of an eye, and a top face opposite the bottom face, and wherein the heating element further comprises a thermally insulating layer disposed on at least the top face of the planar loop but absent from the bottom face of the planar loop.

15. The capsulotomy device of claim 14, wherein the insulating layer is deposited on the heating element by vapor deposition.

16. The capsulotomy device of claim 15, wherein the insulating layer is removed from the bottom face of the planar loop by laser ablation.

17. The capsulotomy device of claim 10, wherein the planar loop has an elliptical shape before deployment in an eye, and wherein the planar loop has a round shape after deployment in the eye.

18. A capsulotomy device comprising:
   a tubular insertion sleeve beveled at a distal end of the tubular insertion sleeve and further comprising two notches disposed opposite one another at the distal end of the tubular insulation sleeve, each of the two notches terminating at the beveled distal end of the tubular insertion sleeve, wherein proximal ends of the notches are vertically asymmetrically offset at the distal end of the tubular insulation sleeve, each of the two notches having a first face and a second face, the first face opposite the second face, wherein the first face extends further distally than the second face; and
   a planar loop located in the two notches, such that when the planar loop is retracted through the two notches, retracted portions of the planar loop cross one another resulting in elevation of the planar loop with respect to the tubular insertion sleeve.

\* \* \* \* \*